(12) United States Patent
Chang (10) Patent No.: US 7,384,388 B2
(45) Date of Patent: Jun. 10, 2008

(54) STYRYL DYES WITH LINKER

(75) Inventor: Young-Tae Chang, New York, NY (US)

(73) Assignee: New York University, New York, NY (US)

( * ) Notice: Subject to any disclaimer, the term of this patent is extended or adjusted under 35 U.S.C. 154(b) by 384 days.

(21) Appl. No.: 11/104,451

(22) Filed: Apr. 13, 2005

(65) Prior Publication Data

US 2005/0227293 A1 Oct. 13, 2005

Related U.S. Application Data

(60) Provisional application No. 60/561,509, filed on Apr. 13, 2004.

(51) Int. Cl.
*C40B 70/00* (2006.01)
*C40B 50/14* (2006.01)
*C12Q 1/00* (2006.01)
*C07D 213/00* (2006.01)

(52) U.S. Cl. .............................. 506/41; 506/30; 435/4; 546/1
(58) Field of Classification Search .................. 506/41, 506/30; 435/4; 546/1
See application file for complete search history.

(56) References Cited

OTHER PUBLICATIONS

Rosania et al., JACS, 2003,125:1130-1131 (published on the Web Jan. 14, 2003).*
Lee et al., Chemical Communications, 15:1852-1853 (2003).*
Li et al., Solid-Phase Synthesis of Styryl Dyes and their Application as Amyloid Sensors, Angew. Chem. Int. Ed. (Nov. 26, 2004), vol. 43, pp. 6331-6335.*

* cited by examiner

*Primary Examiner*—Mark L. Shibuya
(74) *Attorney, Agent, or Firm*—Browdy and Neimark (57) ABSTRACT

A combinatorial library of solid-state fluorescent dyes is prepared by reacting an aldehyde with a solid-supported pyridinium salt having a linker.

3 Claims, 4 Drawing Sheets

Compound code: 2C4

RFU change: 14 fold

A

Compound code: 2D26

**RFU change: 5 fold
$\lambda_{em}$ shift 40nm**

B

Compound code: 2A10

RFU change: 5 fold

Figure 2 Overview of Sensor Chip Development

Figure 3 Fabrication of Linker Dye Chip

A where $R_1$ = various aromatic moeities introduces through adehyde condensation and $R_2$ = various diverse functionalities: alkyl, methoxy, halide, etc.

B where $R_1$ = various aromatic moeities introduces through adehyde condensation and $R_2$ = various diverse functionalities: alkyl, methoxy, halide, etc.

STYRYL DYES WITH LINKER

CROSS-REFERENCE TO RELATED APPLICATION

This application claims priority from provisional application Ser. No. 60/561,509, filed Apr. 13, 2004, the entire contents of which are herby incorporated by reference.

FIELD OF THE INVENTION

The present invention relates to solid-phase combinatorial synthesis of a fluorescent toolbox and use of these compounds as molecular probes.

BACKGROUND OF THE INVENTION

Fluorescent compounds are important compounds because of their broad applications, and particularly because of their highly sensitive and specific detection methods. It is desirable to obtain fluorescent compounds that fluoresce in a wide range of colors so that specific compounds can be selected for different purposes. Rational design of compounds with specific emission wavelengths and high quantum yields is difficult.

Combinatorial chemistry is a synthetic strategy that produces diverse, usually large, chemical libraries. It is the systematic and repetitive, covalent connection of a set of different monomeric building blocks of varying structure to each other to produce an array of diverse molecules. It also encompasses other chemical modifications, such as cyclizations, eliminations, cleavages, etc., that are carried out in a manner that generates permutations and thus collections of diverse molecules.

Chemical combinatorial libraries are diverse collections of molecular compounds. These compounds are formed using a multi-step synthetic route wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

Combinatorial synthetic and screening techniques can identify lead structures from a variety of library compounds, enhancing the success rate in developing useful new compounds while saving much time in trial and error. Following its application in drug discovery, the combinatorial approach now competes with rational design methods in the field of materials science.

While a combinatorial approach has been used in developing fluorescent libraries, the spectral properties and potential applications of the presently available combinatorial fluorescent libraries are still limited.

There is a great need to develop highly specific and rapid sensors/detectors for a variety of diseases (*Combinatorial Chemistry-Synthesis, Analysis, Screening*, June, Ed.; Wiley-VCH; Weinhein, Germany, 1999). Novel fluorescent libraries, which can recognize many different biological analytes and change their fluorescence properties, are of great interest. (Wurthner et al., *Angew. Chem. Int. Ed,* 1999, 38: 1649; Takasu et al., *J. Comb. Chem*, 2003, 5:211; Briehn et al., *Angew. Chem. Int. Ed.,* 2001, 40: 4680; Szurdoki et al., *Anal. Chem.* 2000, 72:5250; Merrington et al., *Chem. Commun.,* 2002, 140-141) Solid phase combinatorial synthesis and screening can identify lead structures from a variety of library compounds, enhancing success rate in developing fluorescent molecules while saving time.

SUMMARY OF THE INVENTION

It is an object of the present invention to overcome the aforesaid deficiencies in the prior art.

It is another object of the present invention to provide a solid-phase combinatorial synthesis of a wide color range of fluorescent compounds.

It is still another object of the present invention to provide fluorescent molecules which are useful as molecular probes.

The fluorescent library of the present invention is based on the styryl scaffold (Rosania et al., *J. Am. Chem. Soc.* 2003 125: 1130-1131), synthesized by the condensation of aldehydes and solid-supported pyridinium salts with different lengths of carbon linkers.

Example of the aldehydes that can be used are shown as R2 in Table 3, and examples of the pyridinium salts that can be used are shown as R1 in Table 2. Example of the linkers are shown in Table 1, scheme 1.

The aldehyde building blocks are commercially available aldehydes containing functionalities of various sizes, conjugation lengths, and electron-donating or withdrawing capabilities. Any aldehyde can be used to prepare the fluorescent compounds.

Based on a synthetic pathway, a fluorescent styryl library was synthesized which was tagged with an intrinsic free amine containing linker using a large set of diversity yielding components.

The entire library was synthesized in both high yield and high purity. The purity of each constituent member was determined by LC-MS prior to screening.

The first library prepared, which had 230 components, yielded compounds from 50-99% purity. The compounds were analyzed for analyte binding using fluorescent plate readers and fluorometers to detect changes in fluorometric properties (intensity and excitation/emission wavelength changes). Among the analytes that can be detected using these fluorescent compounds include DNA, RNA, proteins, carbohydrates, amino acids, metal ions, anions, explosives, etc.

Scheme 1

TABLE 2

R1 Structure

| R1 | Structure |
|---|---|
| A | 4-methylpyridine |
| B | 2-methylpyridine |
| C | 2,6-dimethylpyridine |
| D | 4,4'-dimethyl-2,2'-bipyridine |
| E | 6-methoxy-2-methylquinoline |
| F | 2-methylquinoline |
| G | 4-methylquinoline |

TABLE 3

R2 structure

| R2 | Structure |
|---|---|
| 1 | 2-nitrobenzaldehyde |
| 2 | 2-hydroxy-4-methoxybenzaldehyde |

TABLE 1

Linker structure

| | Linker Structure |
|---|---|
| 6 | $H_2N$–(CH$_2$)$_6$–$R_1$ |
| 2 | $H_2N$–(CH$_2$)$_2$–$R_1$ |

TABLE 3-continued

| R2 | R2 structure Structure |
|----|----|
| 3 |  |
| 4 |  |
| 5 |  |
| 6 |  |
| 7 |  |
| 8 |  |
| 9 |  |
| 10 |  |
| 11 |  |

TABLE 3-continued

| R2 | R2 structure Structure |
|----|----|
| 12 |  |
| 13 |  |
| 14 |  |
| 15 |  |
| 16 |  |
| 17 |  |
| 18 |  |

TABLE 3-continued

R2 structure

| R2 | Structure |
|----|-----------|
| 19 | 3,5-dimethoxy-4-hydroxy... 3,4,5-substituted benzaldehyde with two OMe and one OMe (CHO, OMe, OMe, OMe pattern: 3,4,5-trimethoxybenzaldehyde) |
| 20 | 4-(dimethylamino)benzaldehyde |
| 21 | 2,3,4-trimethoxybenzaldehyde |
| 22 | pyrene-1-carbaldehyde |
| 23 | 3,4-dimethoxybenzaldehyde |
| 24 | 4-formylbenzoic acid |
| 25 | 1-acetyl-1H-indole-3-carbaldehyde |
| 26 | 4-(methylthio)benzaldehyde |
| 27 | 8-formyl-1-naphthoic acid |
| 28 | 4-bromobenzaldehyde |
| 29 | 2-fluorobenzaldehyde |
| 30 | 3-cyanobenzaldehyde |
| 31 | 2-cyanobenzaldehyde |
| 32 | 1-methyl-1H-indole-3,7-dicarbaldehyde |
| 33 | benzo[b]thiophene-3,7-dicarbaldehyde |

TABLE 3-continued

| R2 | Structure |
|----|-----------|
| 34 | benzyl-CHO (phenylacetaldehyde) |
| 35 | 4-cyanobenzaldehyde |
| 36 | 4-nitrocinnamaldehyde |
| 37 | 4-methoxy-1-naphthaldehyde |
| 38 | 4-(diphenylamino)benzaldehyde |
| 39 | 4-isopropylbenzaldehyde |
| 40 | 4-[methyl(2-cyanoethyl)amino]benzaldehyde |
| 41 | 3-phenoxybenzaldehyde |
| 42 | 3-methylbenzaldehyde |
| 43 | 2,5-difluorobenzaldehyde |
| 44 | 1-naphthaldehyde |
| 45 | 4-(1H-imidazol-1-yl)benzaldehyde |
| 46 | 2-methoxycinnamaldehyde |
| 47 | 2-hydroxy-3-methoxybenzaldehyde |

TABLE 3-continued

R2 structure

| R2 | Structure |
|----|-----------|
| 48 |  |
| 49 |  |
| 50 |  |
| 51 |  |
| 52 |  |
| 53 |  |
| 54 |  |
| 55 |  |
| 56 |  |
| 57 |  |
| 58 |  |
| 59 |  |
| 60 |  |
| 61 |  |
| 62 |  |

TABLE 3-continued

| R2 | R2 structure Structure |
|---|---|
| 63 | CHO, phenyl with ortho -O- linkage |
| 64 | CHO, pyridine (2-position CHO) |

DETAILED DESCRIPTION OF THE INVENTION

Fluorescent compounds have attracted attention due to their broad application (Czarnik, Ed, *Fluorescent Chemosensors for Ion and Molecule* Recognition, Washington, D.C., American Chemical Society, 1992; Rettig et al., *Applied Fluorescence in Chemistry, Biology*, and MedicineBerin, Springer-Verlag. Xix, 562, 1991; Slavik, *Fluorescent Probes in Cellular and Molecular Biology*, Ann Arbor, CRC, 1993), coupled with highly sensitive and specific detection methods (Lakowicz, *Principles of fluorescence Spectroscopy*, New York, Klewer Academic/Plenum Publishers, 1999; Herman, *Fluorescence Microscopy*, 2$^{nd}$ ed, New York, Springer, 1998). The fluorescent styryl library of the present invention has great promise as a versatile analyte binding toolbox for sensor development. (Lee et al., *Chem. Commu* 2003, 1852-1853) The library of the present invention provides fluorescent compounds with a handle that can be used in further studies where attachment to a substrate is required, such as microarray or affymatrix materials. The solid phase synthesis of the present invention successfully incorporates a linker that bears a nucleophilic primary amine to the styryl dye library, and effects this with high yield and purity. In addition, the linker composition, which may be of varying length, and free amine group in the end affected a number of properties, including dye performance, solubility, cell permeability, and the spatial relationship between the solid substrate and the linked molecule to fully interact with the target on the solid phase.

The fluorescent styryl libraries of the present invention can be used to develop beta-amyloid peptide sensor molecules. The amyloid diseases, which include Alzheimer's disease, the spongiform encephalopathies, and type II diabetes, are characterized by the abnormal self-assembly and deposition of proteinaceous material into insoluble ordered aggregates (fibrils). (Harper et al., *Annu Rev. Biochem*, 1997, 66:385-407; Bouchard et al., *Protein Science*, 2000, 9:1960-1967) Previously, only Thioflavine T was found to be sufficiently sensitive for detecting amyloid aggregation in solution (Levine, III, *Protein Science*, 1993, 2:404-410).

Eighty compounds from the styryl dye library produced were chosen for the first screening. Five of these compounds showed strong fluorescent emission increase or wavelength shift, as shown in FIGS. 1A-E. All of these compounds exhibited linear response to increasing fibrils concentration. With the highest fibril concentration tested, 1 mg/mL. A maximum 40-fold fluorescent increase and 40 nm shift was observed in the emission wavelength. This result clearly demonstrated the practical use of combining combinatorial synthesis with screening to provide information on selective analyte sensors, in this case, for beta-amyloid peptides.

Figure 1:
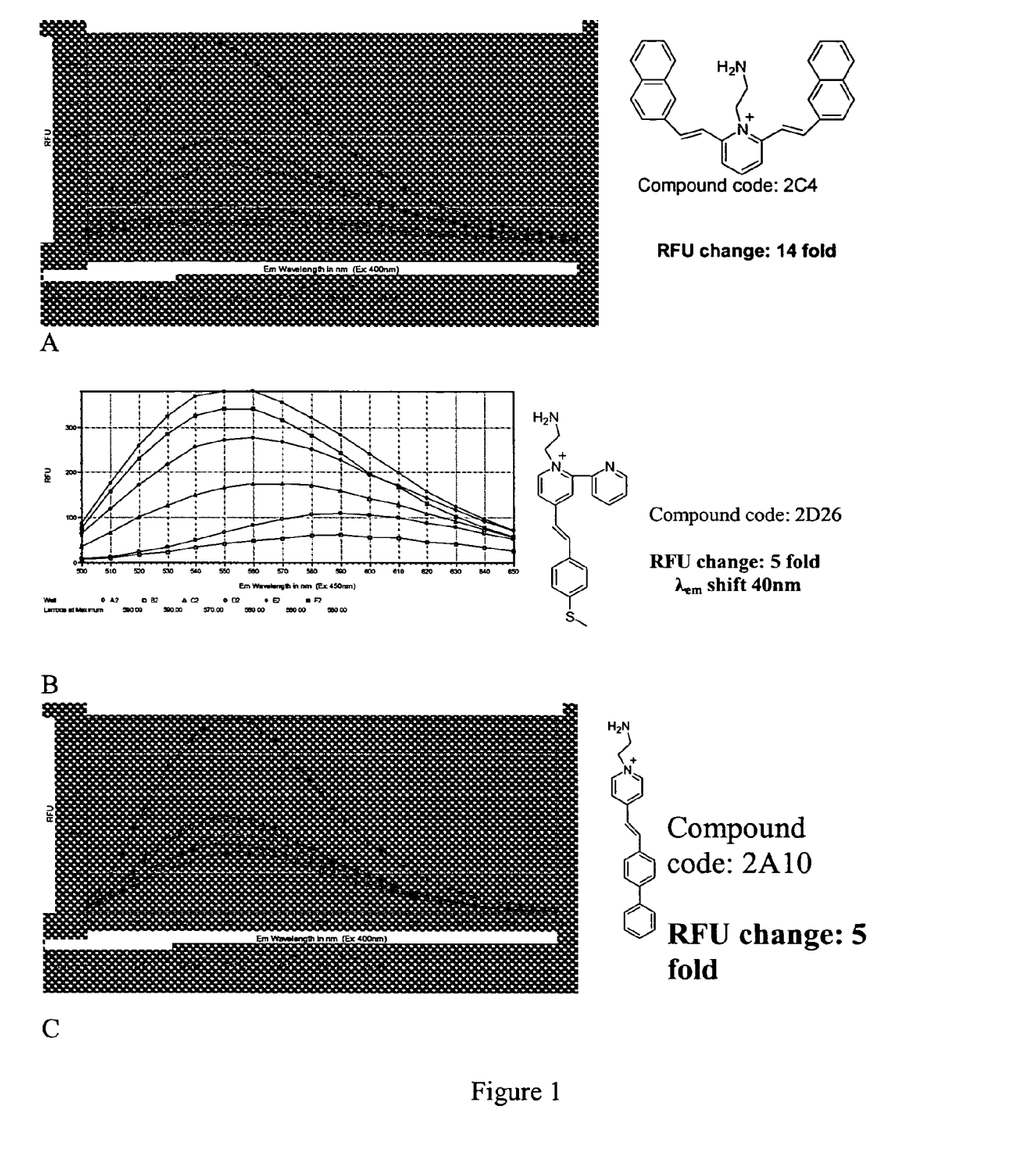
FIGS. 1A, 1B, 1C, 1D, and 1E show beta-amyloid peptides with sensitive dye and sensors.

FIG. 1 shows beta-amyloid peptide sensitive dyes and sensors prepared according to the present invention. Fluorometric titration of the compounds with beta-amyloid peptides in a buffer solution, 1 nmol of compound. The lines in FIGS. 1A-E are as follows:

(compound 1-5 (1 nmol)).

■ Insulin with Fiber 1 mg/ml,
● Insulin with Fiber 0.5 mg/ml,
◇ Insulin with Fiber 0.25 mg/ml
△ Insulin with Fiber 0.125 mg/ml
□ Pure insulin
○ Compound in buffer The fluorescence library of the present invention can be immobilized onto a solid substrate so that primary screening can be performed on the solid phase. Since the libraries contain a free amine via a linker, this functionality is available as a reactive nucleophile in covalent bond forming reactions.

Figure 2:
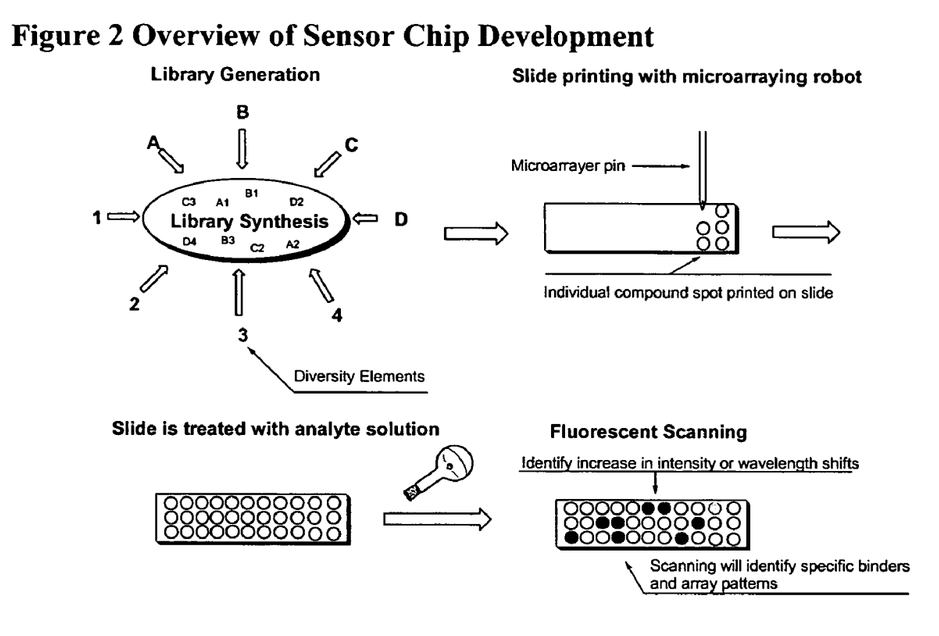
FIG. 2 illustrates development of a sensor chip.

FIGS. 2A-2D illustrate sensor chip development. A library of compounds according to the present invention is generated, with A, B, C, D, 1, 2, 3, and 4 being diversity elements, shown in FIG. 2A. A microarraying robot using a microarrayer pin 20 dispenses compounds onto a slide 21 so that individual compounds 22 are printed onto the slide. In FIG. 2C, the slide 21 is treated with analyte solution. Fluorescent light is directed toward the slide, and as shown in FIG. 2D, scanning will identify specific binders and array patterns.

Figure 3:
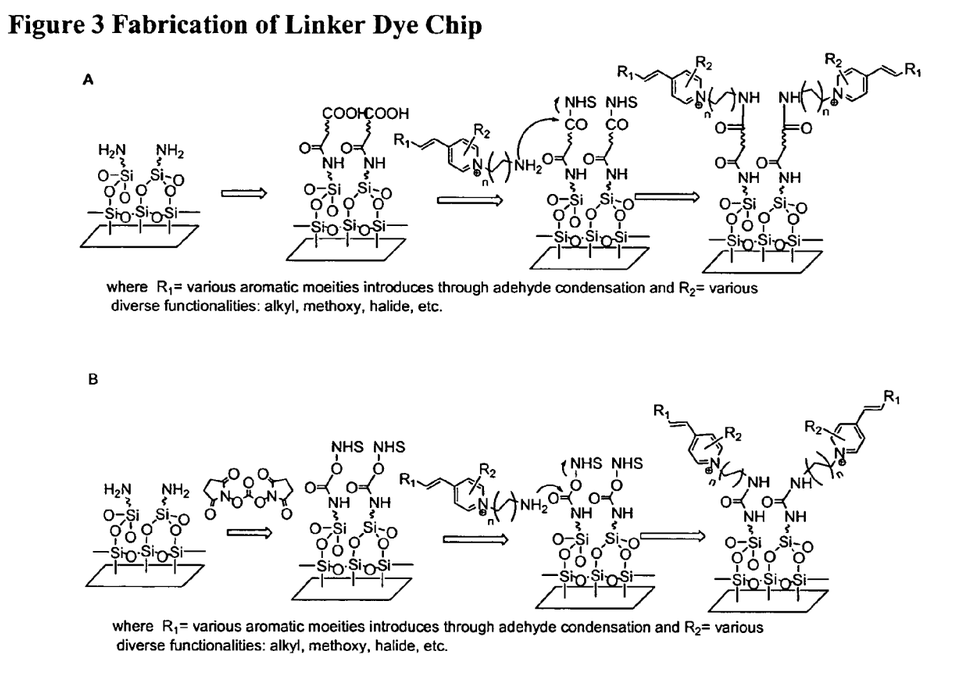
FIGS. 3A and 3B shows fabrication of a linker dye chip.

Immobilization of the compounds of the present invention onto a microarray substrate, in this illustration a derivatized standard glass microscope slide, is easily effected, as shown in FIGS. 3A and 3B. Since the compounds contain a free nucleophilic amine, they are able to react with an active ester fictionalized (NHS) microarray slide surface, forming a covalent bond.

The slides are prepared from standard glass microscope slides from commercial suppliers. The slides are cleaned in an acid/peroxide solution and are aminosilylated by a reaction with (3-amino-propyl)diethoxymethylsilane in toluene. Of course, any other suitable derivatizer that reacts with a free nucleophilic amine can be sued. From this point, two routes are available.

Route 1, shown in FIG. 3A, involves the acid functionalization of the amino slide by reaction with succinic anhydride. The slide was then converted to the active ester (NHS) surface by a coupling reaction with N-hydroxysuccinimide (Lue et al., *Protein Microarrays*, 2003 Jones and Bartlett Publishing.

An alternate route is shown in FIG. 3B. This is a more direct approach, and converted the amino slide to the amine reactive ester slide through direct reaction with N,N'-disuccinimidyl carbonate.

Printing was accomplished by a standard microarraying robot. The dyes were printed in dimethylsulfoxide (DMSO)

and allowed to incubate overnight. Printing solution concentrations were variable and were optimized for each application. After incubation overnight, the remaining reactive NHS groups were "blocked" (i.e., deactivated) by soaking in an aqueous basic solution of ethanolamine. The slides were then washed with double distilled water.

With both of the above routes, thousands of spots per side, on the order of about 10,000 spots per slide, have been produced.

The slides were incubated with the target analyte solution in a relevant buffer at varying concentrations. This incubation can be effected by using cover slips or by a hybridization station used in DNA microarrays. The slides were then washed in the appropriate buffer and dried by centrifugation or by blowing with a nitrogen gas stream. The slides were then scanned for fluorescent intensity in a microarray scanner. The scanner may be of any type, such as laser or CCD, and the slides were scanned for multiple data points at various wavelengths and analyzed. Any analyte dependent response of an independent spot or of the array considered more globally, is significant.

The fluorescent compounds can be applied in yet another way. An alternate route to covalent immobilization is to print the library in discrete nanoliter drops on the surface in a solution of extremely high vapor pressure and low volatility, such as DMSO. The analyte solution may be sprayed onto the surface of the chip in a not perturbative fashion, such as from an aerosolized mist. (Gosalia et al., Proc. Natl. Acad. Sci., 2003 100(15), 8271-8726). In this method, washing is not required, and the chips may be scanned as usual for fluorescent intensity at various wavelengths.

The substituents on the pyridinium salts include substituted and unsubstituted alkyl, alkenyl, alkynyl, and alkoxy, as well as halide and hydroxy. The aldehyde has the formula R—CHO, wherein R is selected from the group consisting of substituted or unsubstituted alkyl, alkenyl, alkynyl, aryl, alkaryl, heterocyclic, cyclic, and fused aryl compounds.

As used herein, alkyl, alkenyl and alkynyl carbon chains, if not specified, contain from 1 to 20 carbon atoms, preferably from 1 to 16 carbon atoms, and are straight or branched. Alkenyl carbon chains of from 1 to 20 carbon atoms preferably contain 1 to 8 double bonds; the alkenyl carbon chains of 1 to 16 carbon atoms preferably contain from 1 to 5 double bonds.

Alkynyl carbon chains of from 1 to 20 carbon atoms preferably contain 1 to 8 triple bonds, and the alkynyl carbon chains of 1 to 16 carbon atoms preferably contain 1 to 5 triple bonds. The alkyl, alkenyl, and alkynyl groups may be optionally substituted, with one or more groups, preferably alkyl group substituents that may be the same or different. As used herein, lower alkyl, lower alkenyl, and lower alkynyl refer to carbon chains having fewer than or equal to about 6 carbon atoms.

As used herein an alkyl group substituent includes halos, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl.

For the present invention, "cyclic" refers to cyclic groups preferably containing from 3 to 19 carbon atoms, preferably 3 to 10 members, more preferably 5 to 7 members. Cyclic groups include hetero atoms, and may include bridged rings, fused rings, either heterocyclic, cyclic, or aryl rings.

The term "aryl" herein refers to aromatic cyclic compounds having up to 10 atoms, including carbon atoms, oxygen atoms, sulfur atoms, selenium atoms, etc. Aryl groups include, but are not limited to, groups such as phenyl, substituted phenyl, naphthyl, substituted naphthyl, in which the substituent is preferably lower alkyl, halogen, or lower alkyl. "Aryl" may also refer to fused rings systems having aromatic unsaturation. The fused ring systems can contain up to about 7 rings.

An "aryl group substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

"Cycloalkyl" as used herein refers to a saturated mono- or multicyclic ring system, preferably of 3 to 10 carbon atoms, more preferably from 3 to 6 carbon atoms. Cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged, or spiro-connected fashion, and may be optionally substituted with one or more alkyl group substituents.

The term "heteroaryl" for purposes of the present application refers to a monocyclic or multicyclic ring system, preferably about 5 to about 15 members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolyinyl and isoquinolinyl.

The term "heterocyclic" refers to a monocyclic or multicyclic ring system, preferably of 3 to 10 members, more preferably 4 to 7 members, where one or more, preferably 1 to 3, of the atoms in the ring system is a heteroatom, i.e., an atom that is other than carbon, such as nitrogen, oxygen, or sulfur. The heterocycle may be optionally substituted with one or more, preferably 1 to 3, aryl group substituents. Preferred substituents of the heterocyclic group include hydroxy, alkoxy, halo lower alkyl. The term heterocyclic may include heteroaryl. Exemplary heterocyclics include, for example, pyrrolidinyl, piperidinyl, alkylpiperidinyl, morpholinyl, oxadiazolyl, or triazolyl.

The nomenclature alkyl, alkoxy, carbonyl, etc, is used as is generally understood by those of skilled this art. As used herein, aryl refers to saturated carbon chains that contain one or more carbon atoms; the chains may be straight or branched or include cyclic portions or may be cyclic.

The term "halogen" or "halide" includes F, Cl, Br, and I. This can include pseudohalides, which are anions that behave substantially similarly to halides. These compounds can be used in the same manner and treated in the same manner as halides. Pseudohalides include, but are not limited to, cyanide, cyanate, thiocyanate, selenocyanate, trifluoromethyl, and azide.

The term "haloalkyl" refers to a lower alkyl radical in which one or more of the hydrogen atoms are replaced by halogen, including but not limited to, chloromethyl, trifluoromethyl, 1-chloro-2-fluoroethyl, and the like.

"Haloalkoxy" refers to RO— in which R is a haloalkyl group.

The term "sulfinyl" refers to —S(O)—. "sulfonyl" refers to —S(O)$_2$—.

"Aminocarbonyl" refers to —C(O)NH$_2$.

"Alkylene" refers to a straight, branched, or cyclic, preferably straight or branched, bivalent aliphatic hydrocarbon group, preferably having from 1 to about 20 carbon atoms. The alkylene group is optionally substituted with one or more alkyl group substituents. There may be optionally inserted along the alkylene group one or more oxygen, sulfur, or substituted or unsubstituted nitrogen atoms, wherein the nitrogen substituent is alkyl. Exemplary alkylene groups include methylene, ethylene, propylene, cyclohexylene, methylenedioxy, and ethylenedioxy. The term "lower alkylene" refers to alkylene groups having from 1 to 6 carbon atoms. Preferred alkylene groups are lower alkylene, with alkylene of 1 to 3 atoms being particularly preferred.

The term "alkenylene" as used herein refers to a straight, branched or cyclic, preferably straight or branched, bivalent aliphatic hydrocarbon group, preferably having from about 1 to 20 carbon atoms and at least one double bond. The alkenylene group is optionally substituted with one or more alkyl group substituents. There may be optionally inserted along the alkenylene group one or more oxygen, sulfur, or substituted or unsubstituted nitrogen atoms, where the nitrogen substituent is alkyl as previously described.

As used herein, "alkynylene" refers to a straight, branched or cyclic bivalent aliphatic hydrocarbon group having from 1 to about 20 carbon atoms and at least one triple bond. The alkynylene group is optionally substituted with one or more alkyl group substituents. There may be optionally inserted along the alkynylene group one or more oxygen, sulfur, or substituted or unsubstituted nitrogen atoms, where the nitrogen substituent is alkyl. The term "lower alkynylene" refers to alkynylene groups having from 2 to 6 carbon atoms.

The term "arylene" as used herein refers to a monocyclic or polycyclic bivalent aromatic group preferably having from 1 to 20 carbon atoms and at least one aromatic ring. The arylene group is optionally substituted with one or more alkyl group substituents. There may be optionally inserted around the arylene group one or more oxygen, sulfur, or substituted or unsubstituted nitrogen atoms, where the nitrogen substituent is alkyl.

"Heteroarylene" refers to a bivalent monocyclic or multicyclic ring system, preferably of about 5 to about 15 members, wherein one or more of the atoms in the ring system is a heteroatom. The heteroarylene may be optionally substituted with one or more aryl group substituents.

As used herein, "alkylidene" refers to a bivalent group, such as =CR'R", which is attached to one atom of another group, forming a double bond. "Arylalkylidene" refers to an alkylidene group in which either R' or R" is an aryl group.

As used herein, when any particular group, such as phenyl or pyridyl, is specified, this means that the group is substituted or unsubstituted. Preferred substituents, where not specified, are halo, halo lower alkyl, and lower alkyl.

The term "library" refers to a collection of diverse compounds, in the present case, based upon a styryl scaffold.

According to the present invention, an aldehyde is reacted with a 2- or 4-methylpyridinium salt in the presence of a secondary amine catalyst in a solvent such as a mixture of DMSO-ethanol. The secondary amine catalysts are exemplified by pyrrolidine or piperidine. However, any secondary amine can be used as a catalyst.

It is to be understood that the phraseology or terminology employed herein is for the purpose of description and not of limitation. The means and materials for carrying out disclosed functions may take a variety of alternative forms without departing from the invention. Thus, the expressions "means to . . . " and "means for . . . " as may be found the specification above, and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above, and it is intended that such expressions be given their broadest interpretation.

REFERENCES

1. *Combinatorial Chemistry-Synthesis, Analysis, Screening*; Jung, G. Ed.; Wiley-VCH: Weinheim, Germany, 1999.
2. (a) Frank Wurthner et al, *Angew. Chem., Int. Ed.* 1999, 38, 1649; (b) Kiyosei Takasu, et al, *J. Comb. Chem.*, 2003, 5, 211; (c). Christoph A. Briehn et al, *Angew. Chem. Int. Ed.*, 2001, 40, 4680; (d). Ferenc Szurdoki et al, *Anal. Chem.*, 2000, 72, 5250; (e). James Merrington et al, *Chem. Commun.*, 2002, 140-141.
3. Combinatorial approach to organelle-targeted fluorescent library based on the styryl scaffold, Rosania, G. R.; Lee, J. W.; Ding, L.; Yoon, H. S.; Chang, Y. T.* *J. Am. Chem. Soc.* 2003,125, 1130-1131.
4. (a).Czarnik, A. W., Ed.;, *Fluorescent Chemosensors for Ion and Molecule Recognition*, Washington, DC: American Chemical Society, 1992; (b). Rettig, W.; Strehmel, B.; Schrader, J.; Seifert, H., *Applied Fluorescence in Chemistry, Biology and Medicine*, Berlin; New York: Springer-Verlag. xix, 562, 1999. (c). Slavik, J., *Fluorescent Probes in Cellular and Molecular Biology*, Ann Arbor: CRC, 1993.
5. (a). Lakowicz, J. R., *Principles of Fluorescence Spectroscopy*, New York: Klewer Academic/Plenum Publishers, 1999; (b) Herman, B., *Fluorescence Microscopy*. 2nd ed., New York: Springer, 1998.
6. Development of novel cell-permeable DNA sensitive dyes using combinatorial synthesis and cell based screening, Lee, J. W.; Jung, M.; Rosania, G. R.; Chang, Y. T.* *Chem Comm* 2003, 1852-1853.
7. (a). James D. Harper; Peter T. Lansbury, Jr., *Annu. Rev. Biochem,* 1997, 66: 385-407; (b). Mario Bouchard et al, *Protein Science,* 2000, 9: 1960-1967.
8. Harry LeVine, III, *Protein Science,* 1993, 2: 404-410.
9. Schidel, M. S.; Briehn, C. A.; Baüerle, P. *Angew. Chem. Int. Ed.* 2001, 40, 4677-4680.

10. Zhu, Q.; Yoon, H. S.; Parikh, P. B.; Chang, Y. T.; Yao, S. Q. *Tetrahedron Lett.* 2002, 43, 5083-5086.
11. Lavastre, O.; Illitchev, I.; Jegou, G.; Dixneuf, P. H. *J. Am. Chem. Soc.* 2002, 124, 5278-5279.
12. Combinatorial approach to organelle-targeted fluorescent library based on the styryl scaffold, Rosania, G. R.; Lee, J. W.; Ding, L.; Yoon, H. S.; Chang, Y. T.* *J. Am. Chem. Soc.* 2003, 125, 1130-1131.
13. Combinatorial fluorescent library based on the styryl scaffold, Chang, T. Y.; Rosania, G. R., U.S. patent applied, 2002.
14. Lue, Y. P. R.; Yeo, S. Y. D.; Tan, L. P.; Uttamchandani, M.; Chen, G. Y. J.; Yao, S. Q. *Protein Microarrays,* 2003: Jones and Bartlett Publishing.
15. Gosalia, D. N.; Diamond, S. L. *Proc. Natl. Acad. Sci.* 2003, 100(15), 8721-8726.

What is claimed is:

1. A method for preparing a combinatorial library of fluorescent dyes comprising reacting an aldehyde with a solid-supported pyridinium salt having a linker.

2. The method according to claim 1 wherein the linker comprises a nucleophilic primary amine having from 2 to 8 carbon atoms.

3. The method according to claim 1 wherein the aldehyde has the formula R—CHO, wherein R is selected from the group consisting of substituted or unsubstituted alkyl, alkenyl, alkynyl, aryl, alkaryl, heterocyclic, cyclic, and fused aryl compounds.

* * * * *